United States Patent [19]

Teunissen et al.

[11] Patent Number: 4,880,929

[45] Date of Patent: Nov. 14, 1989

[54] PROCESS FOR PREPARING A 2-ALKYL-1,4,5,6-TETRAHYDROPYRIMIDINE

[75] Inventors: Antonius J. J. M. Teunissen, Geleen; Willem Klop, Limbricht; Hubertus J. A. V. Delahaye, Voerendaal, all of Netherlands

[73] Assignee: Stamicarbon B.V., Geleen, Netherlands

[21] Appl. No.: 97,657

[22] Filed: Sep. 16, 1987

[30] Foreign Application Priority Data

Dec. 12, 1986 [NL] Netherlands ............... 8603168

[51] Int. Cl.$^4$ .................. C07D 239/26; C07D 239/36
[52] U.S. Cl. ...................................... 544/242; 544/298
[58] Field of Search .................... 544/242, 298

[56] References Cited

U.S. PATENT DOCUMENTS

| | | | |
|---|---|---|---|
| 2,704,757 | 3/1955 | Dornfeld | 544/298 |
| 3,041,338 | 6/1962 | Phillips | 544/298 |
| 3,050,523 | 8/1962 | Erner et al. | 544/242 |
| 4,376,201 | 3/1983 | Pews | 544/242 |
| 4,667,034 | 5/1987 | van de Moesdijk et al. | 544/242 |
| 4,719,299 | 1/1988 | van der Stoel | 544/242 |

FOREIGN PATENT DOCUMENTS 0193973 9/1986 European Pat. Off. ............ 544/242

Primary Examiner—Mukund J. Shah
Assistant Examiner—Diana G. Rivers
Attorney, Agent, or Firm—Cushman, Darby & Cushman

[57] ABSTRACT

The invention relates to a process for preparing a 2-alkyl-1,4,5,6-tetrahydropyrimidine with the formula

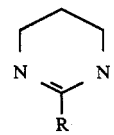

where R represents a straight or branched chain with 1–8 C-atoms or a phenyl group from 1,3-diaminopropane and an alkanecarboxylic acid, in which the alkyl group of such an acid is the same as the R group described above, wherein the starting materials are reacted in the gas phase in the presence of an oxide catalyst at a temperature of between 250° and 450° C. and from the reaction mixture thus obtained the 2-alkyl-1,4,5,6-tetrahydropyrimidine is recovered.

13 Claims, No Drawings

PROCESS FOR PREPARING A 2-ALKYL-1,4,5,6-TETRAHYDROPYRIMIDINE

The invention relates to a process for preparing a 2-alkyl-1,4,5,6-tetrahydropyrimidine with the formula

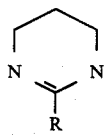

where R represents a straight or branched chain with 1-8 C-atoms or a phenyl group from 1,3-diaminopropane and an alkanecarboxylic acid, in which the alkyl group of such an acid is the same as the R group described above.

Such a process is known from the European patene application EP-A-117882. In this reference a two-step synthesis for preparing 2-t.butyl-1,4,5,6-tetrahydropyrimidine is described via the intermediate product of 3-aminopropylpivalamide. That process concerns a liquid phase process in which the yield over the two steps is 81% (90% x 90%, see example I of EP-A-117882).

Applicant has now found that 2-alkyl-1,4,5,6-tetrahydropyrimidines can be prepared in one step in a comparable or higher yield.

The process according to the invention for preparing a 2-alkyl-1,4,5,6-tetrahydropyrimidine with the formula

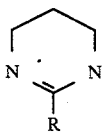

where R represents a straight or branched chain with 1-8 C-atoms or a phenyl group from 1,3-diaminopropane and an alkanecarboxylic acid, in which the alkyl group of such an acid is the same as the R group described above, is characterized in that the starting materials are reacted in the gas phase in the presence of an oxide catalyst at a temperature of between 250° and 450° C. and from the reaction mixture thus obtained the 2-alkyl-1,4,5,6-tetrahydropyrimidine is recovered. The advantage of the process according to the invention is that the preparation takes place in one step. As a result, the process according to the invention can in principle be carried out continuously in a simple manner, which constitutes a cost advantage, in part because no further processing of the linear product of condensation need be carried out between two steps.

In EP-A-117882 it is recommended, on page 3, to use 1,3-diaminopropane (hereinafter referred to as DAP) in a 3-10 mole excess (on pivalic acid). Applicant has surprisingly found that in the process for preparing 2-t.butyl-1,4,5,6-tetrahydropyrimidine according to the invention also a smaller molar excess of DAP on the relative acid may suffice, viz. a molar ratio of 1.5-2.5. As a result, it is easier, of course, to isolate the desired product from the reaction mixture. In addition, it has been found that, when using this preferred ratio, the yield of 2-t.butyl-1,4,5,6-tetrahydropyrimidine has strongly increased.

In addition to 1,3-diaminopropane, =2-hydroxy-1,3-diaminopropane can be used as starting material as well. In that case the resulting reaction product is the 2-alkyl-5-hydroxy-1,4,5,6-tetrahydropyrimidine.

What alkanecarboxylic acid is used in the process according to the invention depends on what alkyl group is desired in the end product. If, for istance, 2-t.butyl-1,4,5,6-tetrahydropyrimidine is to be repared, pivalic acid is started from. If the 2-methyl analogon is to be prepared, acetic acid will be started from. Generally, alkanecarboxylic acids with the formula R-COOH can be started from, in which the R group can be found back as alkyl group at the 2-site in the end product. This R group generally contains 1-8 C atoms and may be aliphatic, as well as aromatic. Suitable acids are, for instance, acetic acid, propionic acid, pivalic acid, (iso)-butyric acid and benzoic acid. The concept of alkanecarboxylic acid is in this connection understood also to mean an ester, anhydride and/or an acid halide of such an acid, such as, for instance, the C 1-4 alkylesters of the above-mentioned acids, as well as the acid chlorides and acid bromides of those acids.

The process according to the invention is carried out in the gas phase. The temperature may vary within wide limits, for instance between 250° and 450° C. The pressure at which the reaction is carried out is of no particular importance as long as the gas phase is maintained in combination, of course, with the temperature. Generally the process will be carried out at autogenous pressure.

In addition to the starting materials, a gas, for instance nitrogen and/or hydrogen, may be introduced into the reactor in order to make the evaporation proceed evenly.

The reaction takes place in the presence of an oxide catalyst. Examples of such oxide catalysts, which must have an oxidizing and/or dehydrating effect, are the oxides of elements from groups 3, 4 and/or 5 of the Periodic System. Particularly the oxides of aluminium and zirconium, possibly in combination with phosphoric acid (ester), are important for a high yield.

The process according to the invention can advantageously be extended to include the preparation of the corresponding 2-alkylpyrimidines by passing the reaction mixture in the gas phase over a second catalyst bed after the formation of the 2-alkyl-1,4,5,6-tetrahydropyrimidine without removal of water between times. This second catalyst must have a dehydrogenating activity. As such the customary supported catalysts are eligible such as, for instance, those of group 8 of the Periodic System. The second catalyst system used is preferably palladium on alumina. These catalysts generally contain 0.1-10% (wt) palladium, preferably 0.5-5% (wt), calculated on the total catalyst. Also an alkali metal may be added to the catalyst in amounts ranging between 0.01 and 2% (wt) calculated on the total catalyst.

The dehydrogenation catalyst can be applied on a carrier known per se. Such carriers may contain, for instance, alumina, carbon and silicon oxide.

In itself a one-step gas phase process for preparing 2-alkylpyrimidine from DAP and an alkanecarboxylic acid(derivative) is known from US-A-3050523. According to this reference, however, the yield of this one-step process is not beyond 35%. In the two-step realization of the present invention a very much higher yield in the order of 90% can be achieved.

For the practical realization of the process according to the invention the modes of realizing gas phase reactions known per se are eligible, for instance the mode of realization in which the gaseous starting mixture is passed over the catalyst in the form of a fixed bed or a so-called fluid bed. The space velocity can be varied, for instance between 0.01 and 10 g starting compound per milliliter catalyst material (bulk volume) per hour.

The further processing of the 2-alkyl-1,4,5,6-tetrahydropyrimidine obtained in the reaction can be effected in a manner known per se by cooling and by, for instance, subsequent distillation or extraction.

The 2-alkyl-1,4,5,6-tetrahydropyrimidines obtained in the process according to the invention can be used as intermediates for the preparation of the corresponding pyrimidines, which in their turn can be used as intermediates for crop protection agents.

The invention is elucidated by means of the following examples:

EXAMPLE I 1,3-diaminopropane and pivalic acid (trimethylacetic acid) were introduced into a vertical tubular reactor (length 400 mm, diameter 20 mm) containing 18 ml catalyst. This catalyst consisted of 98% zirconium oxide and 2% aluminium oxide. The grain size of the catalyst was 3–4 mm. The pivalic acid metering pump, the metering vessel and the feed and outlet pipes were heated to a temperature of 60° C. The acid was metered at a rate of 8.16 grammes per hour. The metering velocity of 1,3-diaminopropane was 5.92 grammes per hour. Besides, hydrogen was introduced into the reactor in an amount of 4 liters pre hour in order to effect an even evaporation of the liquids. The reaction in the gas phase was carried out at a catalyst bed temperature of 340° C. The reaction.gas was scrubbed using 12 grammes methanol per hour, condensed (O° C.) and collected. The amount of 2-t.butyl-1,4,5,6-tetrahydropyrimidine was determined by means of gasliquid chromatography (GLC) in the condensed reaction product collected in two hours' time. The yield of 2-t.butyl-1,4,5,6-tetrahydropyrimidine was calculated on the basis of the amount of 2-t.butyl-1,4,5,6-tetrahydropyrimidine in the reaction product calculated on the amount of pivalic acid metered.

In table 1 the yield of 2-t.butyl-1,4,5,6-tetrahydropyrimidine (t.bu-THP) for different periods of reaction is mentioned in column 1. The percentage of by-products of pivalamide (PA column 2) and 1,3-dipivalamidopropane (DPP column 3) is a measure for the selectivity of the catalyst.

TABLE 1

| Reaction period before sampling × 1 hour | 1 % t.bu-THP | 2 % PA | 3 % DPP |
|---|---|---|---|
| 4 | 78 | 0.5 | 13 |
| 24 | 82 | 0.5 | 12 |
| 44 | 82 | 0.4 | 12 |
| 76 | 81 | 0.5 | 12 |

EXAMPLE II

In the manner described in example I an experiment was carried out for 6 hours in which the amount of 1,3-diaminopropane metered was varied in respect of the amount of pivalic acid. Of the amount of reaction product collected from the 4th up to and including the 6th hour the yields were determined. The results are shown in table 4.

TABLE 2

| Molar ratio 1,3-diaminopropane: pivalic acid | 1 % t.bu-THP | 2 % PA | 3 % DPP |
|---|---|---|---|
| 1.0 | 82 | 0.3 | 13 |
| 1.5 | 92 | 0.2 | 1.5 |
| 2.0 | 95 | 0.1 | 0.1 |
| 3.0 | 95 | 0.1 | <0.1 |

COMPARATIVE EXAMPLE A (Liquid pahse experiment)

Pivalic acid and 1,3-diaminopropane were heated in an autoclave for three hours at 240° C. in the proportion mentioned in the table. On analysis of the reaction mixture a substantial amount of DPP was found to have been formed, see table 3.

TABLE 3

| Molar ratio 1,3-diaminopropane: pivalic acid | Selectivity (DPP % on PVA) |
|---|---|
| 1 | 40.3 |
| 2 | 18.6 |

EXAMPLE III

In the manner described in example I = 2-t.butyl-5-hydroxy-1,4,5,6-tetrahydropyrimidine was prepared from a salt mixture consisting of 2 moles 2-hydroxy-1,3-diaminopropane and 1 mole pivalic acid.

The results are shown in table 4.

TABLE 4

| Reaction period × 1 hour | % yield based on pivalic acid 2-t.bu-5-hydroxy-1,4,5,6-tetrahydropyrimidine |
|---|---|
| 4 | 70 |
| 8 | 72 |
| 12 | 72 |

EXAMPLE IV

The experiment of example I was required using, instead of pivalic acid, an equivalent amount of acetic acid. The results after a number of hours are shown in table 5.

TABLE 5

| Reaction period × 1 hour | % yield of 2-methyl-1,4,5,6-tetrahydropyrimidine |
|---|---|
| 4 | 75 |
| 8 | 80 |
| 16 | 88 |
| 24 | 89 |

EXAMPLE V

To the catalyst bed described in example I a second catalyst bed was linked consisting of 16 ml 1% Pd on alumina. Over this double-bed system 79 mmoles/hour 1,3-diaminopropane and 41 mmoles/hour pivalic acid were passed at 340° C. and under an inflow of 14 l hydrogen gas per hour. The 2-t.butyl-pyrimidine yield was determined by means of GLC. This yield was 90.4 moles %.

EXAMPLE VI

In the manner described in example I =2-phenyl-1,4,5,6-tetrahydropyrimidine was prepared from 1,3-diaminopropane and benzoic acid in a molar ratio of 2:1. After three hours the yield of 2-phenyl-1,4,5,6-tetrahydropyrimidine was 70% calculated on benzoic acid.

We claim:

1. Process for preparing a 2-alkyl-1,4,5,6-tetrahydropyrimidine with the formula

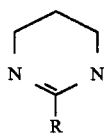

where R represents a straight or branched chain with 1-8 C-atoms or a phenyl group from 1,3-diaminopropane and an alkanecarboxylic acid, in which the alkyl group of such an acid is the same as the R group described above, wherein the starting materials are reacted in the gas phase in the presence of a metal oxide catalyst having an oxidizing or dehydrating effect and wherein said metal oxide catalyst includes a metal or metals selected from the group consisting of the elements of groups 3, 4 and 5 of the periodic system, at a temperature of between 250° and 450° C. and from the reaction mixture thus obtained the 2-alkyl-1,4,5,6-tetrahydropyrimidine is recovered.

2. Process according to claim 1, wherein the chosen alkanecarboxylic acid is pivalic acid or acetic acid.

3. Process according to claim 2, wherein 1,3-diaminopropane and pivalic acid are used in a molar ratio of between 1.5:1 and 2.5:1.

4. Process according to claim 1, wherein the catalyst used includes a metal or metals selected from the group consisting of aluminum and zirconium.

5. Process according to claim 1, wherein the reaction is carried out in the presence of hydrogen and/or nitrogen.

6. Process for preparing a 2-alkyl-5-hydroxy-1,4,5,6-tetrahydropyrimidine with the formula

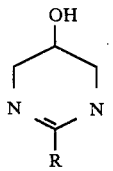

where R represents a straight or branched chain with 1-8 C-atoms or a phenyl group, in which process 2-hydroxy-1,3-diaminopropane and an alkanecarboxylic acid, in which the alkyl group of such an acid is the same as the R group described above, are reached in the gas phase in the presence of a metal oxide catalyst having an oxidizing or dehydrating effect and wherein said metal oxide catalyst includes a metal or metals selected from the group consisting of the elements of groups 3, 4 and 5 of the periodic system, at a temperature of between 250° and 450° C. and from the reaction mixture obtained the 2-alkyl-5-hydroxy-1,4,5,6-tetrahydropyrimidine is recovered.

7. Process according to claim 6, wherein the chosen alkanecarboxylic acid is pivalic acid or acetic acid.

8. Process according to claim 7, wherein 2-hydroxy-1,3-diaminopropane and pivalic acid are used in a molar ratio of between 1.5:1 and 2.5:1.

9. Process according to claim 6, wherein the catalyst used includes a metal or metals selected from the group consisting of aluminum and zirconium.

10. Process according to claim 6, wherein the reaction is carried out in the presence of hydrogen and/or nitrogen.

11. Process for preparing a 2-alkylpyrimidine with the formula

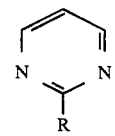

where R represents a straight or branched chain with 1-8 C-atoms or a phenyl group from 1,3-diaminopropane and an alkanecarboxylic acid, in which the alkyl group of such an acid is the same as the R group described above, wherein in the first step the starting materials are reacted in a gas phase in the presence of a metal oxide catalyst having an oxidizing or dehydrating effect and wherein said metal oxide catalyst includes a metal or metals selected from the group consisting of the elements of groups 3, 4 and 5 of the periodic system, at a temperature of between 250° and 450° C. and subsequently, in a second step, the reaction mixture obtained is dehydrogenated in the gas phase in the presence of a dehydrogenating catalyst including an element of group 8 at a temperature of between 250° and 400° C. and finally, from the reaction mixture obtained in the second step, the 2-alkylpyrimidine is recovered.

12. Process according to claim 11, wherein the dehydrogenating catalyst used is a noble metal from group 8 of the Periodic System.

13. Process according to claim 12, wherein the dehydrogenating catalyst used is palladium on alumina.

* * * * *

UNITED STATES PATENT AND TRADEMARK OFFICE
CERTIFICATE OF CORRECTION

PATENT NO. : 4,880,929

DATED : November 14, 1989

INVENTOR(S) : TEUNISSEN et al.

It is certified that error appears in the above-identified patent and that said Letters Patent is hereby corrected as shown below:

Column 1, line 20, please correct "patene" to read --patent--;
column 2, line 3, please delete "=";
column 2, line 10, please correct "repared" to read --prepared--;
column 3, line 35, please correct "pre" to read --per--;
column 4, line 15, please correct "pahse" to read --phase--;
column 4, line 32, please delete "="; and
column 5, line 3, please delete "=".

Signed and Sealed this

Ninth Day of October, 1990

Attest:

HARRY F. MANBECK, JR.

*Attesting Officer*                *Commissioner of Patents and Trademarks*